US00PP28245P3

(12) United States Plant Patent
Olesen

(10) Patent No.: US PP28,245 P3
(45) Date of Patent: Aug. 8, 2017

(54) CLIMBING ROSE PLANT NAMED 'POULCY029'

(50) Latin Name: ***Rosa* hybrid**
Varietal Denomination: Poulcy029

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 14/121,271

(22) Filed: Aug. 15, 2014

(65) Prior Publication Data

US 2016/0050804 P1 Feb. 18, 2016

(51) Int. Cl.
*A01H 5/02* (2006.01)

(52) U.S. Cl.
USPC ..... Plt./114

(58) Field of Classification Search
USPC ..... Plt./114
CPC ..... A01H 5/0222; A01H 5/0216
See application file for complete search history.

(56) References Cited

PUBLICATIONS http://www.poulsenroser.dk/media/73071/COURTYARD-Climbers-2013_LR_Poulsen-Roser.pdf; 2012; 1 page.*

* cited by examiner

*Primary Examiner* — Kent L Bell

(57) ABSTRACT

A new garden rose plant of the Climbing class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulcy029'.

SUMMARY OF THE INVENTION

The present invention constitutes a new and distinct variety of garden rose plant which originated from a controlled crossing between the female seed parent, an unnamed, non-patented, seedling, and the male pollen parent, also an unnamed, non-patented, seedling.

The two parents were crossed during the summer of 2004 and the resulting seeds were planted in a controlled environment in Fredensborg, Denmark. The new variety, named 'Poulcy029', originated as a single seedling from the stated cross.

The new variety may be distinguished from its male pollen parent and female seed parent primarily by growth habit. The female seed parent has a floribunda rose growth habit, compared to the new plant's climbing habit. The male pollen parent is a compact floribunda, approximately 40 cm in height.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.
4. Reduced apical dominance in flowering habit with characteristics of a climbing rose. The new variety consistently produces flowers evenly from the lower branches to the top of the plant.

This combination of qualities is not present in previously available commercial cultivars of this type, known to the inventor, and distinguish 'Poulcy029' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulcy029' was selected in the spring of 2005 by the inventor as a single plant from the progeny of the aforementioned hybridization.

Asexual reproduction of 'Poulcy029' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulcy029' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy029'.

Specifically illustrated in FIG. 1 are open flowers at various stages of development, and flowers in parts.

Figure 1:
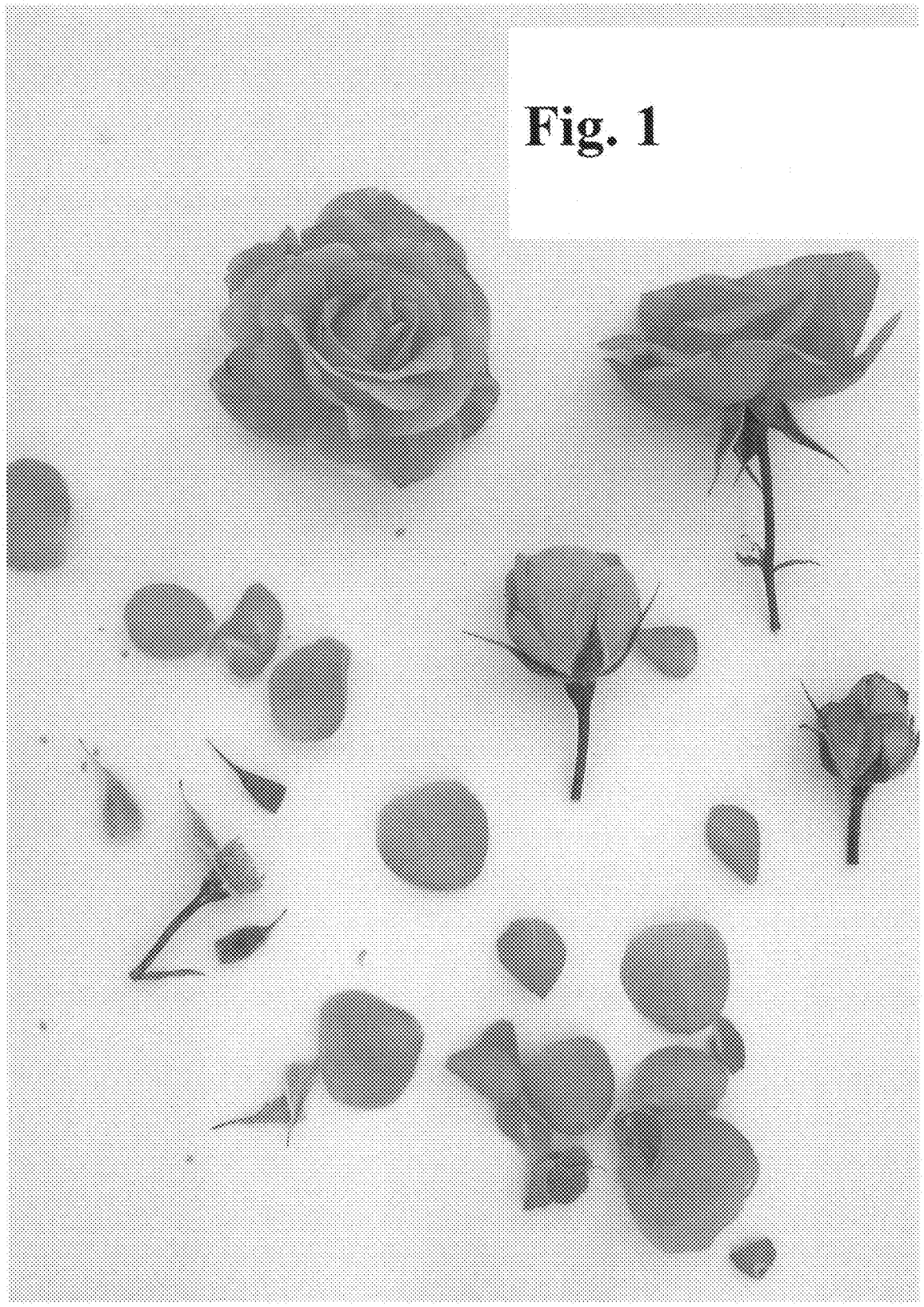
Figure 2:
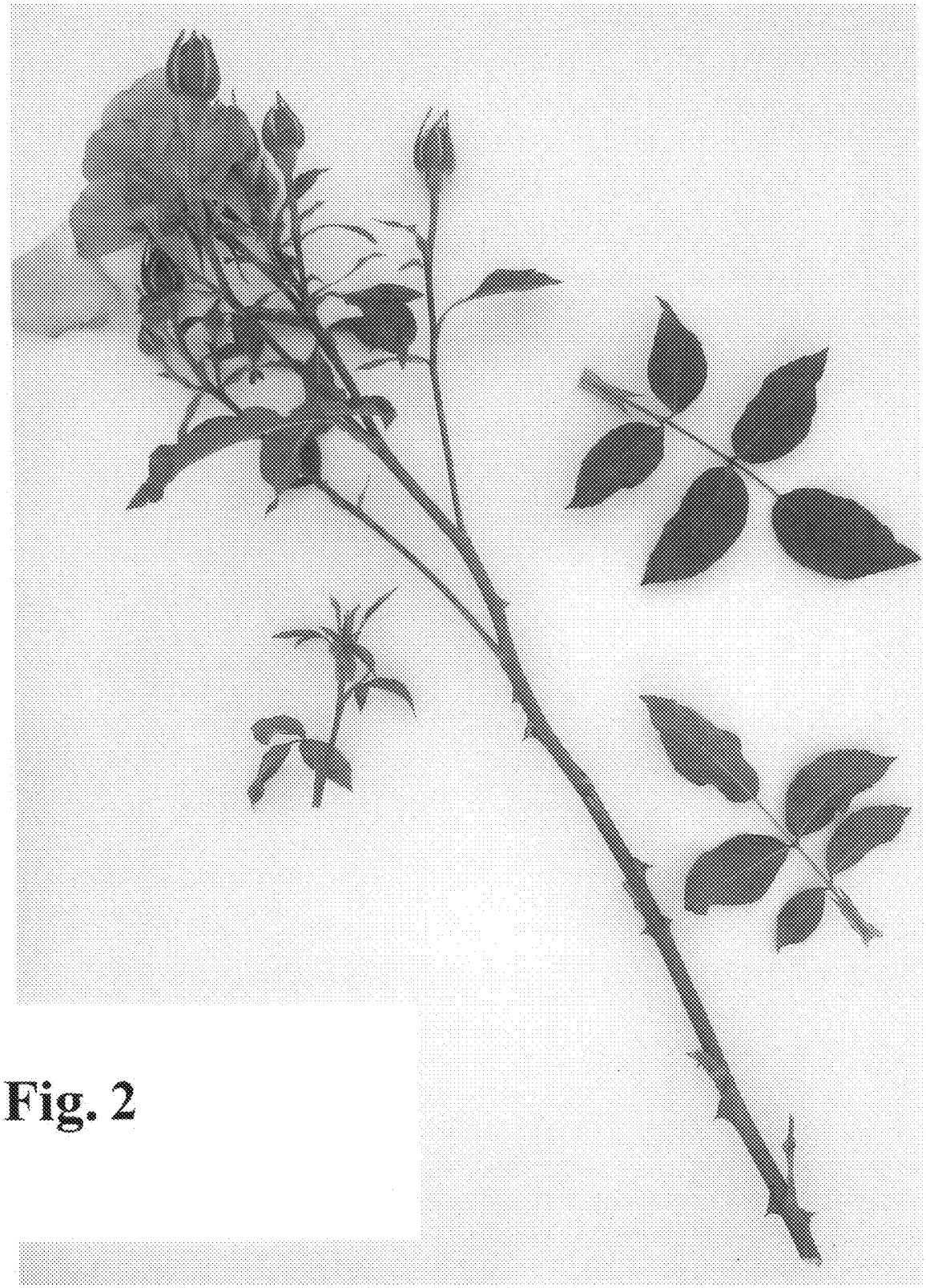

Specifically illustrated in FIG. 2 are leaves, stems, and a flowering branch.

Illustrated plants are 2 years of age.

DETAILED DESCRIPTION OF THE VARIETY

The following is a description of 'Poulcy029', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcy011', U.S. Plant Pat. No. 16,584 are compared to 'Poulcy029' in Chart 1.

CHART 1

| | 'Poulcy029' | 'Poulcy011' |
|---|---|---|
| General Tonality of Flower Color | Red Group 55A to Red-Purple Group 62A | Red-Purple Group 62C to 62D with intonations of Red-Purple Group 58C |
| Flower Diameter | 65 mm | 45-55 mm |
| Petal Count | 35 | 60 |

FLOWER AND FLOWER BUD

Blooming habit: Continuous.

Flower bud:

*Size.*—Upon opening, 25 mm in length from base of receptacle to end of bud. Bud diameter is 15 mm.

*Bud form.*—Ovoid.

*Bud color.*—As sepals divide petals are Orange-Red Group N34C.

*Sepal inner surface.*—Color: Yellow-Green Group 144A. Surface: Smooth and pubescent.

*Sepal outer surface.*—Color: Yellow-Green Group 144A with light intonations of Greyed-Orange Group 176A. Texture: Smooth with stipitate glands.

*Sepal shape.*—Apex: Cirrhose. Base: Flat at union with receptacle.

*Sepal margin.*—Margins have weak foliaceous appendages on three of the five sepals.

*Sepal size.*—23 mm long by 9 mm wide.

*Receptacle.*—Texture: Smooth. Size: 6 mm in height by 6 mm wide. Color: Yellow-Green Group 146C with light intonations of Greyed-Orange Group 166A. Shape: Campanulate.

*Pedicel.*—Surface: Smooth. Length: 35 mm. Diameter: 2 mm on average. Color: Yellow-Green Group 146C with strong intonation of Greyed-Purple Group 184B. Strength: Strong.

*Peduncle.*—Length: 5 to 25 cm. Diameter: 4 mm. Color: Yellow-Green Group 144A with strong intonations of Greyed-Red Group 178A.

Flower bud development: Flower buds are borne in clusters of 15 to 20 flower buds per stem, resembling a panicle. Reduced apical dominance in flower habit causes flower buds develop evenly from the base of the plant to the upper portion.

Flower bloom:

*Fragrance.*—Moderate perfume.

*Duration.*—The blooms have a duration on the plant of approximately 7 to 10 days. Petals fall cleanly away from plant after flowers have fully matured.

*Size.*—Flower diameter is 65 mm when open. Flower depth is 30 mm.

*Flower shape.*—General shape is hybrid tea like.

*Shape of flower, side view.*—The upper portion is flat. The lower portion is flattened convex.

Petalage: Under normal conditions, flowers have 35 petals total, 5 of which are petaloids.

General tonality of flower: Open flowers are Red Group 55A to Red-Purple Group 62A.

Petal color:

*Upon opening, outer petals.*—Upper surface: Red Group 55B. Yellow Group 10B petal spot. Lower surface: Red Group 55B. Yellow Group 10B petal spot.

*Upon opening, inner petals.*—Upper surface: Red Group 43C. Yellow Group 10B petal spot. Lower surface: Red Group 48C. Yellow Group 10B petal spot.

*After opening, inner and outer petals.*—Upper surface: Red Group 55A. Yellow Group 10B petal spot. Lower surface: Red Group 55B. Yellow Group 10B petal spot.

Petals:

*Petal reflex.*—Lightly reflexed.

*Margin.*—Entire. Weak undulations of margin observed.

*Shape.*—Generally broad elliptic. Apex shape: Rounded. Base shape: Acute.

*Size.*—37 mm (l) 35 mm (w).

*Texture.*—Smooth.

*Thickness.*—Above average.

Petaloids:

*Size.*—10 mm (l) by 6 mm (w).

*Quantity.*—5 on average.

*Shape.*—Base is acute. Apex is rounded with a cleft.

*Color.*—Red Group 43B upper. Lower is Red Group 43C. Yellow 10B petal spot on upper and under surface.

Reproductive organs:

*Pollen.*—None observed.

*Anthers.*—Size: 2 mm in length. Color: Yellow-Orange Group 20A. Quantity: 30 on average.

*Filaments.*—Color: Yellow Group 13C. Length: 4 mm.

*Pistils.*—Length: 7 mm. Quantity: 15 on average.

*Stigmas.*—Color: Yellow-Green Group 154D.

*Styles.*—Color: Yellow-Green Group 154D.

*Location of stigmas.*—Superior in location relative to the length of the filaments and the height of the anthers.

*Hips.*—None Observed.

PLANT

Plant growth: Climbing and bushy. Plants are 90 cm in height, and 75 cm wide.

Stems:

*Color.*—Juvenile growth: Yellow-Green Group 146D with anthocyanin Greyed-Red Group 178B. Mature growth: Yellow-Green Group 144A.

*Length.*—On average, canes are 30 cm from the base of the plant to the flowering portion.

*Diameter.*—10 mm.

*Internodes.*—On mature canes, there is an average distance of 40 mm between nodes.

*Surface texture.*—Young wood: Smooth. Older wood: Smooth.

Long prickles:

*Incidence.*—10 prickles per 10 cm of stem.

*Size.*—Average length of prickles on mature stems is 6 mm.

*Shape.*—Upper portion is linear. Lower portion is concave.

*Color*.—Juvenile prickles: Greyed-Purple Group 183B. Mature prickles: Greyed-Yellow Group 160A.

Plant foliage:

*Compound leaf*.—160 mm (l)×112 (w).

*Quantity*.—2 leaves per 10 cm of stem on average.

*Color of juvenile foliage*.—Upper side: Greyed-Orange Group 175A. Lower side: Greyed-Orange Group 175A.

*Color of mature foliage*.—Upper side: Yellow-Green Group 147A. Lower side: Yellow-Green Group 147B.

Plant leaves and leaflets:

*Stipules*.—Size: 30 mm in length. Quantity: 2 per compound leaf. Shape: Linear, slightly broad based with outward extending apices. Margins: Finely serrated. Color: Yellow-Green Group 144A.

*Petiole*.—Length: 30 mm. Diameter: 1 mm.

*Upper surface*.—Color: Yellow-Green Group 144B with Greyed-Red Group 178C.

*Lower surface*.—Color: Yellow-Green Group 144A.

*Rachis*.—Length: 55 mm. Upper surface: Color: Yellow-Green Group 144B with Greyed-Red Group 178C.

*Lower surface*.—Color: Yellow-Green Group 144A.

Leaflet:

*Quantity*.—Normal number of leaflets leaves in middle of the stem is 5 leaflets.

*Margins*.—Serrated.

*Size*.—Average size of the terminal leaflet on normal leaves is 80 mm in length by 42 mm wide.

*Shape*.—Generally lanceolate. Base: Rounded. Apex: Acute.

*Texture*.—Smooth.

*Thickness*.—Average.

*Arrangement*.—Odd pinnate.

*Venation*.—Reticulate.

*Glossiness*.—Moderately glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticultural Society heat zone 7.

The invention claimed is:

1. A new and distinct variety of rose plant of the Climbing rose class named 'Poulcy029', substantially as illustrated and described herein, due to its abundant pink flowers, disease resistance, and extended period of bloom.

* * * * *